United States Patent [19]

Smith et al.

[11] Patent Number: 4,842,701

[45] Date of Patent: Jun. 27, 1989

[54] COMBINED ELECTROPHORETIC-SEPARATION AND ELECTROSPRAY METHOD AND SYSTEM

[75] Inventors: Richard D. Smith, Richland; José A. Olivares, Kennewick, both of Wash.

[73] Assignee: Battelle Memorial Institute, Richland, Wash.

[21] Appl. No.: 34,875

[22] Filed: Apr. 6, 1987

[51] Int. Cl.[4] .............................................. B01D 57/02
[52] U.S. Cl. .............................. 204/180.1; 204/183.3; 204/299 R; 436/173; 250/281; 250/288
[58] Field of Search ............. 204/180.1, 183.3, 299 R; 436/173; 250/288 R, 288 A, 281

[56] References Cited

U.S. PATENT DOCUMENTS

| | | | |
|---|---|---|---|
| 4,144,451 | 3/1979 | Kambara | 250/281 |
| 4,160,161 | 7/1979 | Horton | 250/281 |
| 4,209,696 | 6/1980 | Fite | 250/288 |
| 4,531,056 | 7/1985 | Labowsky et al. | 250/288 |
| 4,542,293 | 9/1985 | Fenn et al. | 250/288 |
| 4,647,772 | 3/1987 | Lewis et al. | 250/288 |
| 4,705,616 | 11/1987 | Andresen et al. | 204/299 R |
| 4,708,782 | 11/1987 | Andresen et al. | 204/299 R |

FOREIGN PATENT DOCUMENTS

84302751.7   4/1984   European Pat. Off. .

OTHER PUBLICATIONS

"Negative Ion Production with the Electrospray Ion Source", M. Yamashita & J. B. Fenn, The Journal of Physical Chemistry, vol. 88, Nov. 20, 1984, pp. 4671–4675.
"Capillary Zone Electrophoresis", J. W. Jorgenson, et al., Science, vol. 222, pp. 266–272, Oct. 1983.
"Electrospray Interface for Liquid Chromatographs and Mass Spectrometers", C. M. Whitehouse, et al., Anal. Chem., pp. 675–679, 03/85.
"Microcolumn High Performance Liquid Chromatography", P. Kurcera, Ed., The Journal of Chromatography Library, vol. 28, Amsterdam, 1984.
"Electrospray Mass Spectroscopy of Macromolecule Degradation in the Electrospray", D. Teer & M. Dole, The Journal of Polymer Science: Polymer Physics Edition, vol. 13, pp. 985–995, 1975.
"Electrospray Mass Spectroscopy of Maromolecules: Application of an Ion Drift Spectrometer", J. Gieniec, et al., 10 pages.
"Electrospray Ion Source. Another Variation on the Free-Jet Theme", M. Yamashita & J. B. Fenn, The Journal of Physical Chemistry, pp. 4451–4459, 1984.
"Detectors for Use with Small Bore Columns", Small Bore Liquid Chromatography Columns: Their Properties & Uses, Raymond P. W. Scott, Ed., vol. 72, John Wiley & Sons, New York 1984.
"Mixed Zone Analysis in Isotachophoresis with Selective Detection by Mass Spectrometry Applied to the Quantitation of Hydrogenation Products of Aromatic Quanternary Ammonium Compounds", Anal. Chem., pp. 391–396, 1985.
Dole, Malcolm; Mack, L. L.; and Hines, R. L., "Molecular Beams of Macroions", Journal of Chemical Physics, vol. 49, No. 5, pp. 2240–2249, Sep. 1, 1968.

(List continued on next page.)

Primary Examiner—John F. Niebling
Assistant Examiner—Kathryn Gorgos
Attorney, Agent, or Firm—Marger & Johnson

[57] ABSTRACT

A system and method for analyzing molecular constituents of a composition sample includes: forming a solution of the sample, separating the solution by capillary zone electrophoresis into an eluent of constituents longitudinally separated according to their relative electrophoretic mobilities, electrospraying the eluent to form a charged spray in which the molecular constituents have a temporal distribution; and detecting or collecting the separated constituents in accordance with the temporal distribution in the spray. A first high-voltage (e.g., 5–100 KVDC) is applied to the solution. The spray is charged by applying a second high voltage (e.g., ±2–8 KVDC) between the eluent at the capillary exit and a cathode spaced in front of the exit. A complete electrical circuit is formed by a conductor which directly contacts the eluent at the capillary exit.

41 Claims, 6 Drawing Sheets

OTHER PUBLICATIONS

Mack, L. L.; Kralik, P.; Rheude, A., and Dole, M., "Molecular Beams of Macroions.II", Journal of Chemical Physics, vol. 52, No. 10, pp. 4977–4986, May 15, 1970.

Clegg, G. A. and Dole, M., "Molecular Beams of Macroions, III. Zein and Polyvinylpyrrolidone", Biopolymers, vol. 10, pp. 821–826, 1971, John Wiley & Sons, Inc.

Andresen, Brian D. and Fought, Eric R., "Electrophoretic Mass Spectrometry", Lawrence Livermore National Laboratory FY 86 Institutional Report (UCRL-53689-86).

Jorgenson, James W., "Capillary Zone Electrophoresis", Chapter 13 in New Directions in Electrophoretic Methods, American Chemical Society, Washington, D.C., 1987, pp. 182–198.

COMBINED ELECTROPHORETIC-SEPARATION AND ELECTROSPRAY METHOD AND SYSTEM

The U.S. Government has rights in this invention in accordance with the operating contract DE-AC06-76RLO 1830 between Battelle Memorial Institute and the U.S. Department of Energy.

BACKGROUND OF THE INVENTION

This invention relates to a method and apparatus for analyzing chemical compositions and more particularly to a method and system for combining free zone electrophoretic separation of a mixture sample with electrospraying to interface with on-line detection or off-line collection apparatus.

Numerous systems employed in the separation and analysis of analytes are known in the prior art. However, these prior art systems are not necessarily broadly applicable to the separation and/or analysis of analytes which comprise complex materials, or high molecular weight, nonvolatile, and highly polar compounds.

One known method for separation of analyte mixtures, free zone electrophoresis in small diameter capillaries or capillary zone electrophoresis (CZE), is used for a wide variety of analyses including high resolution separations of amino acids, peptides, proteins and complex salt mixtures. CZE employs a capillary with a electric field gradient to separate the analyte constituents, particularly ions, by difference in electrophoretic mobilities in addition to electroosmotic flow in the capillary. The electroosmotic flow results when an electrical double layer of ions forms at the capillary surface, and an electrical field is imposed lengthwise along the capillary. The field causes the ions to migrate towards the oppositely charged electrode at rates determined by the electrophoretic mobility of each analyte. In the resulting bulk electroosmotic flow, positively charged ions, neutral species, and negatively charged ions elute at different time intervals. The extent and speed of this separation are determined by differences in the electrophoretic mobilities of the analytes, the length of the capillary, the bulk electroosmotic flow and by the strength of electric field.

FIG. 1 is a schematic illustration of the customary arrangement of a CZE system. In this arrangement, a complete high voltage electrical circuit must be formed between opposite ends of the capillary filled with a buffer solution. This is accomplished by immersing both ends of the capillary in beakers of the buffered solutions at each end of the system.

CZE detection is currently limited to analysis by ultraviolet or fluorescent detection techniques, so as not to degrade the quality of the separation. Such detection techniques have been adequate for species that fluoresce, absorb, or are amenable to derivatization with fluorescing or absorbing chromophores. These detectors also impose cell volume and sample size limitations that preclude high separation efficiencies concurrent with high sensitivities. Structural information necessary for the correct identification of unknown analytes and their constituents cannot be obtained using these detectors due to the small sample volume and the limited spectroscopic data inherent in UV and fluorescence detection techniques. These limitations constitute a major drawback in the use of CZE for the separation and identification of complex mixtures since many compounds cannot be detected, and, if detectable, cannot be unambiguously identified. A detailed discussion of CZE can be found in an article by Jorgenson, et al., in the publication "Science" (1983), Vol. 222, beginning at page 266.

A well-known analytical technique which combines a separation technique with an analytical detection device is gas chromatography-mass spectrometry (GC-MS). In this method, GC can provide separations of sufficiently volatile compounds which are then ionized and analyzed by mass spectrometry. GC-MS has become established as the definitive analytical technique for amenable compounds, i.e., compounds having sufficient volatility for GC separation and ionization by conventional gas phase electron impact or chemical ionization methods used in mass spectrometry.

Such an established capability of broad application is not known to exist for nonvolatile compounds and mixtures. Systems for combining liquid chromatography with mass-spectroscopy are described in U.S. Pat. No. 4,209,696 and in European Patent Application 84302751.7, which are incorporated herein by reference. In these systems, carried liquid from a liquid chromatograph is electrosprayed and then analyzed by mass spectrometry. To work, electrospray requires an ionic strength of less than about $10^{-2}$ molar. Various other attempts to combine liquid chromatography with mass spectroscopy are described in "Microcolumn High Performance Liquid Chromatography, P. Kucera, Ed., *J. Chromatography Library*, Vol. 28, Chap. 8, pp. 260–300 (1984) and in "Small Bore Liquid Chromatography Columns: Their Properties and Uses," R.P.W. Scott, ed., Vol. 72, pp. 104–114 (1984). Unfortunately, these systems and other LC-MS approaches suffer significant limitations due to their inability to effectively separate complex mixtures, their limited separation efficiency, and the time required for analysis or separation. Combined liquid chromatography-mass spectroscopy does not provide high resolution separations. In liquid chromatography, the maximum number of theoretical plates is limited to about 10,000 for reasonable separation times (under about one hour). In contrast, CZE has been shown to be able to provide over one million theoretical plates in the same time.

Accordingly, a need remains for a method of separation that has the high-resolution separation of efficiencies of CZE and, additionally, an ability to analyze a wide range of nonvolatile compounds.

SUMMARY OF THE INVENTION

This invention relates to a system and method for interfacing the free zone electrophoretic separation of a sample and electrospray, respectively, so that the molecular constituents of the electrosprayed eluent produced have a temporal distribution and can be concentrated by evaporation of the solvent. The electrosprayed eluent can be subsequently analytically detected on-line using mass spectrometry, or other analysis methods, or can be collected off-line for analysis or other applications requiring highly-purified samples.

A system and method for analyzing molecular constituents of a sample includes: forming a solution of the sample, separating the solution by capillary electrophoresis into an eluent of constituents longitudinally separated according to their relative electrophoretic mobilities, electrospraying the eluent to form a charged spray in which the molecular constituents have a temporal distribution; and detecting or collecting the separated constituents in accordance with the temporal distribution in the spray.

A first high-voltage (e.g., 5–100 KVDC) is initially applied to the solution to separate its constituents. The separated eluent is electrosprayed and the spray is charged by applying a second high voltage (e.g., ±2–8 KVDC) between the eluent at the capillary exit and a counter electrode spaced in front of the exit. A complete electrical circuit is formed by a conductor which directly contacts the eluent at the capillary exit.

Capillary electrophoresis includes variations such as electrokinetic chromatography or isotachophoresis. Electrospraying includes processes which involve electric fields, and may include concurrent utilization of nebulizing gases or heating methods.

The sample can include complex, high-molecular-weight, nonvolatile and highly-polar compounds. Ordinarily, the solution includes a buffering agent. Detection can be by apparatus that does not depend on UV or fluorescence of the constituents and that is capable of identifying and quantifying, or providing universal detection of, the constituents.

The interface includes means for applying a first high voltage potential between the source of sample solution and the capillary outlet, to effect electrophoretic separation in the sample, and means for applying a second high voltage potential between the capillary outlet and the collector or detector, to electrospray and ionize the separated sample as it is discharged. In one embodiment, the capillary outlet end can be metallized to conductively couple the eluent to the second high voltage source.

The invention finds particular advantage in interfacing capillary-zone electrophoresis and mass spectrometry (CZE-MS). In one embodiment of this application, the CZE cathode serves as an electrospray needle for spraying a separated sample into a mass-spectrometer. The analyte eluent at the capillary outlet is biased relative to the mass spectrometer at a voltage potential sufficient to produce the electrospray, which is then sampled by the mass spectrometer. Electrospraying is carried out at near-atmospheric pressure. Accordingly, the mass spectrometer preferably includes a differentially pumped input chamber. The interface can further include an ion lens to aid ion transmission into the detector. It can also include means for desolvating or vaporizing the ionized spray to form an ion vapor phase stream into the mass spectrometer.

The foregoing and other objects, features and advantages of the invention will become more readily apparent from the following detailed description which proceeds with reference to the drawings.

DETAILED DESCRIPTION OF A PREFERRED EMBODIMENT

Description of CZE-Electrospray Interface

Figure 2:
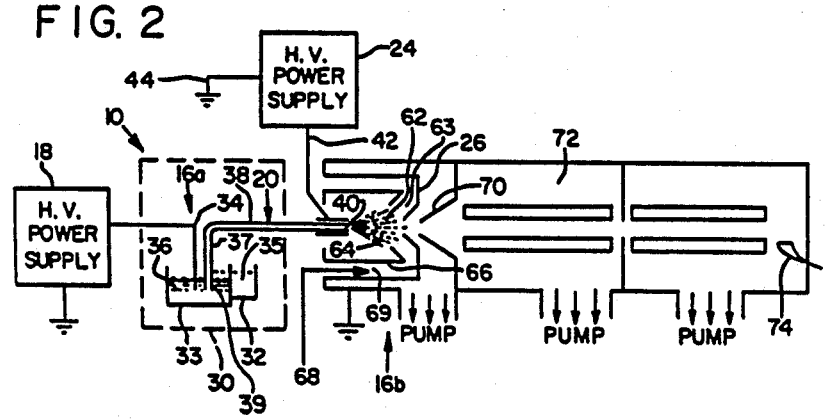
FIG. 2 is a schematic illustration of apparatus for capillary zone electrophoresis-mass spectrometry (CZE-MS) in accordance with the invention.
Figure 2A:
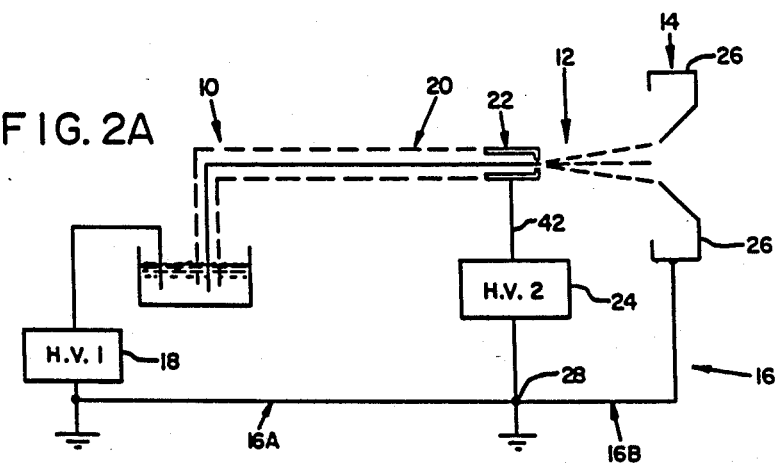
FIG. 2A is an electrical circuit diagram of the apparatus of FIG. 2.

FIG. 2 shows an apparatus for combined CZE-electrospray-mass spectrometer (CZE-MS) in accordance with a preferred embodiment of the present invention. FIG. 2A is an electrical circuit diagram of a generalization of the system of FIG. 2.

Referring first to FIG. 2A, a CZE-electrospray interface according to the invention generally comprises a capillary-zone electrophoresis (CZE) subsystem 10, an electrospray interface 12, a detection of collection device 14, and a high voltage electrical circuit 16. The CZE subsystem 10 and electrospray interface 12 form integral parts of the electrical circuit 16. Specifically, the CZE subsystem forms a part of a subcircuit 16A which includes a first high voltage supply 18 and capillary 20 having an outlet nozzle 22. The electrospray interface forms subcircuit 16B which includes a second high voltage supply 24 and a counterelectrode 26 in the detector/collector 14. The two subcircuits are electrically interconnected at nozzle 22 and node 28, for example, ground. Optionally, a third power supply (not shown) can be used to bias the counterelectrode relative to node 28.

Referring next to FIG. 2, the CZE subsystem 10 includes an electrically insulated sampling box 30, provided to isolate a first high voltage system 16a from the outside environment. For example, a lucite or plexiglass box can be employed for this purpose. From a safety standpoint, this portion of the system is isolated because of the dangers to the user from this high voltage application.

Within box 30 are a sample injection reservoir 32 and a buffer reservoir 33 which contain the analyte sample and the CZE buffer solution in separate containers. High voltage system 16A includes a first high voltage power supply 18 and an electrode or microsampling arm 34 extending into the reservoir 33. An analyte sample solution 35 is formed in reservoir 32 by adding a suitable chemical solvent to a sample of the material to be analyzed. A buffering agent 36 is provided in reservoir 33. Typically, the reservoir to which either solution is added comprises a standard micro-beaker or other liquid container made of glass or the like.

A capillary 20 is also disposed within the sampling box 30. The capillary 20 may have a bend with a vertical inlet section 37 (depending upon sample introduction method) and horizontally-disposed outlet section 38, and includes respective inlet and outlet ends 39 and 40. The capillary inlet end 39 extends into sample solution reservoir 32 during injection of the sample solution 35 and into the buffer solution 36 in reservoir 33 during separation. Outlet end 40 is electrically connected, as hereinafter described, to form a closed electrical circuit for the first high voltage system 16a.

Capillary 20 can be fabricated in the form of any capillary structure capable of effecting the capillary zone electrophoretic process. Particularly, however, nonconductive materials such as glass, fused silica, Teflon® and the like are preferred materials of construction of such capillary. Preferably, the capillary has a length of 20 to 500 centimeters and has an inside diameter which ordinarily ranges from about 25 uM up to about 250 uM, although a wider range of dimensions is feasible.

Capillary tube 20 has joined to its outlet end 40 a second high voltage input system 16B, including a second high voltage power supply 24. This system 16B is grounded or biased at a selected voltage above ground to complete a first closed circuit for high voltage supply 18, as shown in FIG. 2A. The electrical connection at the capillary outlet end serves as both the electrode for the CZE step and also as the spray needle for the electrospray step. More specifically, the system 16B forms a completed circuit with high voltage supply 24 through a physical connection with a high voltage line 42. Thus, high voltage power supply 24 is grounded at one end 44 and is connected at its other end through high voltage line 42 to outlet end 40. This electrical connection also forms circuit 16B, which enables the analyte to be electrosprayed upon application of a second high voltage from voltage supply 24 through line 42.

A large voltage drop is applied from the inlet end 39 to the outlet end 40 of the capillary to enable electrophoretic separation of the analyte solution 36. The high voltage also causes a bulk electroosmotic flow of buffer towards the capillary outlet 40. The high voltage is applied from power supply 18 through microsampling arm 34 into the reservoir 33. The voltage drop along the capillary is the difference between the voltage from supply 18 and the voltage from supply 24. The voltage drop draws the buffer solution 36 into capillary 20. It also causes solution 36 to be electrophoretically separated into its individual molecular constituents as they pass at differing levels of electrophoretic mobility from inlet end 39 to outlet end 40. The amount of voltage provided from power supply 18 into the sample analyte solution 36 ranges typically from about 5 kilovolts DC up to about 100 kilovolts DC. If ions of both positive and negative electrophoretic mobility are to be analyzed, the electroosmotic flow must be sufficiently large to offset the electrophoretic motion in the opposite direction, so that all analytes of interest move towards the capillary exit. It should be noted that nonconducting capillaries can form an electrical double layer with electroosmotic flow in a direction and rate that depends on the surface or any surface treatment of the capillary. In such a situation, the polarity of the voltages required for CZE separation may be reversed.

Figure 3:
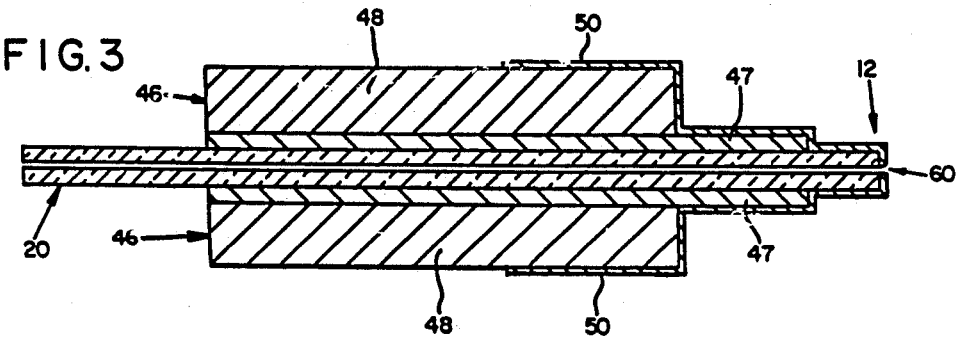
FIG. 3 is a schematic cross-sectional view of the capillary zone electrophoresis cathode which also serves as the electrospray needle in the apparatus of FIG. 2.

The basis of the invention includes forming a completed electrical contact at or near the capillary exit 40 without immersing it in a beaker of solution. Referring to FIG. 3, a schematic illustration of the capillary zone electrophoresis electrode which serves as the electrospray needle, a novel CZE-electrospray interface (ESI) system 12 is provided. The outlet end 40 of capillary 20 has a conductive stainless steel capillary sheath 46 located concentrically thereabout. The sheath 46 comprises respective inner section 47 and outer section 48 joined one to the other. Sheath 46 is attached to capillary 20 by an adhesive such as an epoxy resin or the like. The sheath 46 is physically connected to high voltage power supply 24 by means of a copper conductive wire 42 (see FIGS. 2 and 2A). A conductive metal-plated end section 50 is plated concentrically about the exit of the outlet end 40, including the exit portions of respective sheath sections 47 and 48, to form conductive tip 60 contacting the electrophoretically separated solution 36.

In one form of the invention, a metal coating is sputtered onto the respective exit portion of sheath 46 and outlet end 40 so that electrical contact is directly made with the eluent at tip 60 as soon as it emanates from the exit of nonconductive fused silica capillary 20. Typically, a metal such as gold, silver, or platinum is employed for this purpose. Preferably, the conductive tip is formed so that the dead volume after completion of the electrical circuits is minimized and there is virtually no flow turbulence within capillary 20 and, therefore, no substantial contribution to band broadening (or loss of separation) of the analyte sample. The ability to minimize flow turbulence, and thereby maintain continuous flow of the eluent 36 in capillary 20, is dependent upon capillary diameter and length. For example, the effective dead volume for a 100 um. i.d. capillary 1 M in length should be not more than about 10 nL, and preferably less than about 1 nL.

The electrical contact can be formed in other ways, which include (1) joining a metal capillary to the nonconductive CZE capillary; or (2) electrical contact through a small conductive capillary segment near the capillary exit. The latter can be done in numerous ways, but approaches that minimize the dead volume after the electrical contact are necessary so as to avoid loss of separation efficiency.

High voltage system 16B creates an electrical potential between the capillary tip 60 and eluent 36 and the collection or detection apparatus, such as the counter electrode 26 of the mass spectrometer shown in FIGS. 2 and 2A. The purpose is to produce an electric field resulting in the desired electrospray process.

Depending upon whether positively or negative charged constituents are to be desirably produced by subsequent electrospraying, either a positive or a negative (±) voltage is applied to the capillary end 40 relative to the counter electrode (sampling orifice) 26. Voltages of about ±2,000 to 8,000 volts DC can generally be used, with a voltage of about ±3,000 to 4,000 volts DC being preferred depending upon the distance to the counter electrode. The resultant electric field causes the eluent 36 to be discharged (electrosprayed) in airspace 62 from the conductive tip 60 of capillary tube 20. This produces a fine spray 64 of electrically charged droplets including gaseous ions, solvent and solvent-carrying analyte material, having a charge polarity determined by the field.

Figure 7:
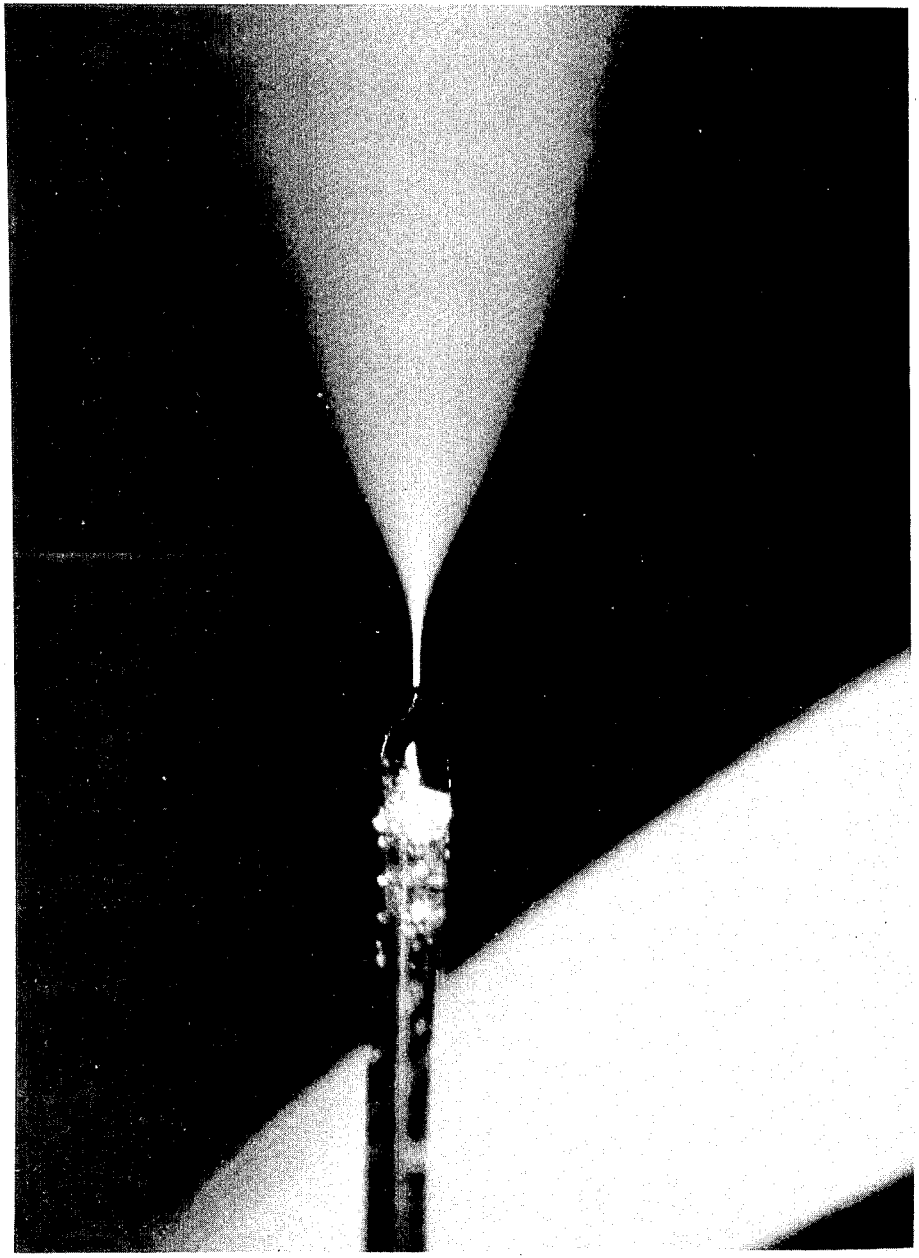
FIG. 7 is a photograph of a fully developed electrospray produced at the end of a fused silica capillary similar to that of FIG. 3.

These electrospray droplets are attracted towards counter electrode 26, which has sampling provisions (i.e., an orifice) for on-line detection or off-line collection device, by the electric filed created by high voltage system B. FIG. 7 shows a photograph of a fully developed electrospray flowing from capillary outlet 40.

Electrospray Analysis

Analysis of the electrosprayed eluent 64 can be conducted employing any on-line detection or off-line collection equipment capable of analyzing the molecular or atomic constituents of the eluent. Alternative analysis techniques are further described hereinafter. Preferably, molecular analysis by on-line detection techniques, and more preferably, by mass spectrometry is employed as next described.

In on-line detection gaseous phase analysis, hereinafter described, a counter-current flow of hot gas is typically used to assist solvent vaporization of the spray 64 of charged droplets. Thus, vapor is removed from the electrospray source region, which is at approximately atmospheric pressure. The resultant droplets have nearly uniform size, similar charge, and produce gaseous molecular ions.

As depicted in FIG. 2, a ring member 66 is employed to heat the gas in the airspace which in turn heats the exiting electrosprayed analyte eluent 64. Generally, gas temperatures of from about 50° C. up to about 120° C. can be employed for this purpose but a wider range of temperatures would be usable depending on flow rate.

A countercurrent gas flow 68 of inert or reactive gases can be employed, along or in combination with the previously-described thermal heating for desolvating the spray droplets. Typical inert gases include nitrogen, helium and the like, and typical reactive gases include ammonia, oxygen and the like. Countercurrent gas flows are directed through chamber 69 so as to impinge the electrosprayed analyte eluent 64 within the airspace 62. Typical gas flow rates of from about 0.1 liter per minute, up to about 20 liters per minute, can be employed for this purpose.

Operation of CZE-Electrospray Interface

The method and system of this invention is broadly applicable to the analysis of any material soluble in water or polar solvents, particular ionized or partially ionized species. Compounds amenable to this process include normally neutral compounds on which a charge can be induced by manipulation of buffer solution composition and neutral compounds separated by buffer solutions containing micellar phases or microemulsions by partitioning between the bulk liquid and micelle phases. This includes materials separable by electrokinetic chromatography, as well as those separable by CZE and capillary isotachophoresis. In general, complete mixtures of positive, negative and neutral constituents in solution are amenable to separation and analysis by the subject invention. This method and system is more particularly applicable to the separation of organic, inorganic, and bio-organic molecules soluble in aqueous solutions. Nonaqueous solvents may also be used. Some organic solvents, especially those with some ionic characteristics, or those that can be seeded or mixed with ionic components, are also applicable. With respect to the solvent portion of the analyte sample solution 36, any solvent is suitable for use herein as long as it exhibits at least a minimum conductivity. The solution 36 preferably has a minimum surface tension, if used with gas phase ion detection methods, in order to permit maximum desolvation on subsequent electrospraying. Thus, compounds ranging from aqueous to organic solvents to mixtures of solvent components may be employed if a certain minimum ionic strength of the analyte solutions formed are achieved. Aqueous sample solutions preferably include a buffering agent. These solutions are preferably provided at concentrations below about 0.01 M.

Buffer materials are also required for most CZE media. The buffer and solvent mixtures are chosen according to the sample employed in the electrophoretic process relative to the buffer selected. The buffer portion of solution 36 provides a number of important properties. First, the buffer imparts ionic strength for enhancing conductivity and minimizing field effects which distort separation of the individual constituents. It also provides a stable pH medium in which the solution is stabilized and effective constituent separations can be performed at different electrophoretic mobility levels. A solution is formed with a sufficient level of conductivity that subsequent electrospraying can be effectively performed. Buffer concentrations preferably ranging from about $10^{-6}$ to about $10^{-2}$ molar are particularly useful in this invention. Typical compounds employed as buffers include ionic salts such as ammonium salts, inorganic salts such as sodium and potassium chloride, and organic salts such as potassium phthalate.

Regarding electrical current present in the system, it should be noted that a high voltage-low current relationship is typically maintained in the system. Currents which will facilitate the system and method of this invention and which can provide maximum separation of the analyte constituents are employed. Although the current is dependent upon such variables as the ionic strength of the solution, the capillary column length and inside diameter of the capillary, current is preferably maintained at or below the 100 uA level. The current is typically directly proportional to voltage and the maximum voltage is usually selected so that heating of the buffer solution in the capillary is minimized, since heating results in convective flow which degrades separation efficiency.

In order to analyze the molecular constituents according to the method and system of the present invention, sample solution 36 is electrophoretically separated into its molecular constituents. The use of electrophoresis according to the teachings of the subject invention facilitates high efficiency separation or analysis of complex materials. First, voltage is briefly applied to the analyte sample solution 36 and migration of a small amount of the sample solution into a capillary 20 is achieved due primarily to electroosmotic flow. The buffer solution reservoir 33 is then introduced into the sampling box 30, the capillary is removed from the sample reservoir and introduced into the buffer reservoir, high voltage is applied thereto, and electrophoresis proceeds.

Electroosmosis is caused by the migration of ions, from the diffusive layer of the electrical double layer at the capillary surface, under the influence of an electrical field imposed tangentially to the surface. The ions present in the analyte will then migrate towards the oppositely charged electrode carrying the capillary contents with them. The electroosmotic flow is sufficiently fast that positively charged ions, neutral molecular compounds, and negatively charged ions elute in short times, typically about 5-30 minutes for a 1 M capillary. In a positive voltage gradient, positive ions will have the largest net mobilities and will elute first since they are repelled by the high voltage anode, resulting in positive electrophoretic mobilities, and also will be carried by the electroosmotic bulk flow of the solvent. Negative ions having the largest negative electrophoretic mobilities will elute last. Negative ions with very high electrophoretic mobilities may never elute from the column if the electroosmotic flow is not sufficiently fast, but usually conditions can be varied so that the electroosmotic mobility is always larger than the analyte's electrophoretic mobility.

Therefore, the migration time through the capillary column 20 is for the most part determined by a combination of the capillary length, the molecule's electrophoretic mobility and the electric field, the electric field strength, and the electroosmotic flow of the supporting buffer solution. The various constituents forming analyte sample 36 have different relative electrophoretic mobilities. These differences in electrophoretic mobility produce a dissimilar rate of migration of the molecular constituents from the inlet 39 to the outlet 40 of capillary 20. This results in an effective, high efficiency separation of these different molecular constituents with respect to time so that the identity and quantity of each constituent can be individually analytically determined or collected.

In defining the optimum conditions for electrophoretic flow of analyte eluent 36 from inlet 39 to outlet 40, the following are some of the preferred conditions: a minimum metal surface contact or other electrical contact between the analyte flowing in the capillary to complete an electrical circuit near the point of electrospray formation, a substantially constant voltage drop from inlet 39 to outlet 40, and a continuous inner flow surface, having minimum discontinuous surface areas and substantially no dead volume is present, so that electroosmotic flow of the analyte eluent 36 in the capillary is created with a minimum introduction of any turbulent effects.

The electrospray of the subject invention can be used in both the positive and negative ionization modes, although a small addition of oxygen or other electron scavenger to the bath gas is useful for negative ion production to avoid electrical breakdown.

For mass spectrometric analysis, this atmospheric pressure ion source is then typically followed by a molecular beam sampling apparatus consisting of a nozzle-skimmer arrangement with an RF only quadrupole field or ion lens system for ion focusing and a quadrupole mass spectrometer for mass analysis and detection. Other mass-spectrometer inlet designs are feasible. For example, nonconductive capillaries can be used as disclosed in Whitehouse, C.M., et al., "Electrospray Interface for Liquid Chromatographs and Mass Spectrometers," Analytical Chemistry, Vol. 57, pp. 675–679 (1985).

In the preferred form of this invention, the electrosprayed droplets are allowed to continually divide and evaporate at near atmospheric pressure to form gaseous ions of analyte constituents employing electro-spray techniques similar to those described in U.S. Pat. No. 4,209,696 and EPA 84302751.7. The solution flow in the capillary results preferably from electroosmotic flow rather than any pressure drop, so that separation efficiency is not degraded. Thus spray 64 is formed without substantial distortion of the electropherogram thereby permitting analysis by numerous analytical detectors.

The electrospray process utilized for mass spectrometric detection is similar to that developed by previous workers. As the droplets are formed by the electrospray process, desolvation of the solvent from the droplets begins to occur, and the analyte constituent passes from the liquid phase into the gaseous phase, the gaseous phase including gaseous ions of the analyte constituents. As the droplets move away from outlet 40, they continually decrease in size and their mass-to-charge ratios continually shrinks until an ionic vapor phase stream is formed which is capable of detection by mass spectrometry. Desolvation of the solvent from its association with the droplets can be facilitated thermally and/or by countercurrent gas flow. Electrospraying includes processes which involve electric fields, and may include concurrent utilization of nebulizing gases or heating methods.

In any case, the desolvated vapor phase ions produced, along with the remaining portion of the analyte present within airspace 62, are conveyed to a mass spectrometer for analyzing the identity and quantity of the individual constituents contained in the analyte sample.

Improvements in Mass Spectrometry for CZE-Mass Spectrometry System

Certain features which improve or facilitate analysis using mass spectrometry have also been uncovered with respect to the analysis of electrosprayed eluent 64. These include, for example, the use of an RF only lens in the first vacuum region of the mass spectrometer. These lenses are known to provide nearly 100 percent containment of ions in triple, quadrupole mass spectrometers, where the lens is operated in an intermediate vacuum of about $5 \times 10^{-4}$ torr, which is similar to the pressures used in the first vacuum region of the CZE-MS system interface. This RF only lens also acts as a high pass mass filter allowing only ions above a preselected mass of interest to pass into the mass analyzer. This cleansing effect (since high ion currents are to be expected from the buffer employed at low masses) provides spectra which are potentially free of space charge effects created when high ion currents containing ions of no interest to the analyst enter the normal quadrupole mass analyzer and are to be rejected during mass analysis. Quadrupole devices are mass analyzers in the form of mass-to-charge separators.

A well-coupled RF-RF/DC pair of quadrupole lenses is also employed to minimize the fringe field effects observed when the lens combination is DC-RF/DC. This serves to maximize ion transmission into the mass analyzer.

Finally, the use of quartz inlet capillaries to transmit ions from the atmospheric pressure electrospray ionization source is a feasible alternative to the nozzle-skimmer introduction method which allows the direct injection of transmitted ions into the RF only quadrupole.

Alternative Analytical Applications

The electrospray interface also provides a basis for combining CZE separations with other on-line analysis techniques. In these methods, the electrospray is sample so that either the small liquid droplets or gas phase ions are introduced into an analytical or detection device. Thus, this invention includes the combination of free zone electrophoresis (and variations which include electrokinetic chromatography and isotachophoresis) separation methods, using electro-spray, with other detection methods which include:

1. flame ionization detection;
2. elemental analysis by inductively-coupled plasma of microwave plasma atomic emission for elemental analysis;
3. ion mobility detection;
4. photo ionization detection;

5. element-specific ionization detection;
6. electron capture detection;
7. surface-sensitive analytical methods;
8. infrared analysis of electrosprayed deposits.

The common feature of all the above analysis methods is that a gaseous or aerosol sample is required. The electrospray process produces such a gas or aerosol which may be interfaced to these detection devices. Each analysis method requires somewhat different methods for sampling the electrospray. However, the methods are such that someone reasonably skilled in the above techniques, given the information disclosed herein, could successfully combine CZE with the selected analytical method. It should be noted that some methods will present difficulties due to limited sensitivities, and thus may impose some limitations upon the practice of CZE (such as the use of a larger than optimum sample that may degrade separation efficiency) or the analytical detection method.

Off-line collection or analysis methods are also feasible using the electrospray. In these methods the electrospray is collected on a solid or liquid surface. The surface can be moved so that the temporal distribution of separated analytes is deposited on the surface as a spatial distribution. The separated sample collected on the surface can be utilized for other offline analysis methods or other purposes where only a small sample is required. The spatially distributed material can also be analyzed by analytical methods which are compatible with solid samples on surfaces. These analytical methods include:

1. mass spectrometry using a moving ribbon or belt with ionization methods which include ion or atom bombardment;
2. infrared analysis of surfaces;
3. any surface-sensitive analytical method.

EXAMPLE

Using the CZE-mass spectrometer system specifically depicted in FIG. 2, the identity and quantity of an analyte sample was determined.

CZE was carried out using a 0-60 kV dc power supply, Glassman High Voltage Inc. (Whitehouse Station, N.J.) Model LG60P2.5. The high voltage electrode and capillary end (anode) and solution vials were contained in an insulating sampling box with a remote controlled sampling arm and injection timer to facilitate the interchange and injection of solutions. Fused silica capillaries, 100 um i.d. and 100 cm long, from Polymicro Technologies, Inc. (Phoenix, AZ), were used in all experiments without further treatment. The cathode (low voltage end) of the fused silica capillary was terminated in a stainless steel capillary sheath, 300 um i.d. and 450 um o.d. (see FIG. 3). The sheath potential was controlled with a 0 to 5 kV dc power supply and functions as both the CZE cathode and electrospray needle (see FIG. 2A).

Electrospray ionization was carried out at atmospheric pressure in a 2.54 cm long by 2.29 cm i.d. stainless steel cylinder. The cylinder terminated in an electrically biased (190 V dc) focusing ring 44 with a 0.475 cm aperture. The ion sampling orifice (or nozzle) 63 had a 0.5 mm i.d. orifice, was made from copper, which was in contact with a copper cylinder at ground potential. This cylinder surrounded the electrospray assembly and was heated to 60° C. by a system of cartridge heaters (not shown). The electrospray needle, focusing ring 66, and ion sampling nozzle 63 were disposed concentrically with the mass analyzer. These components could be positioned independently relative to the fixed skimmer 70 (with the aid of linear motion drives), even while high voltage is applied, in order to maximize ion formation and transmission. A flow of $N_2$ forming a gas curtain, at a flow rate of 2.5 L/min, is fed between the focusing ring 66 and the nozzle 63 and directed so as to flow counter to the electrospray to aid in the desolvation process.

The vacuum system consisted of a three stage differentially pumped chamber, although many different arrangements are feasible. The first stage allows for a supersonic beam expansion through the ion sampling nozzle 63. This region is pumped to 0.85 Torr by a 150 L/s roots blower. A portion of the supersonic beam is sampled by a 1.2 mm i.d. beam skimmer, Beam Dynamics, Inc. (Minneapolis, MN), Model 1. The second differentially pumped stage houses a 22 cm long, 0.95 cm diameter quadrupole filter 72. This quadrupole is operated in the RF only mode with a $-1.8$ V dc rod bias and acts as an ion lens which facilitates ion transmission to the analysis quadrupole. The presure in this region is maintained at $10^{-4}$ to $10^{-5}$ Torr with a 1500 L/s turbomolecular pump. Another version of this instrument substituted an integral cryo-pump which provided a pumping speed of approximately 50,000 L/S and allowed larger orifice and skimmer diameters. An electrically isolated stainless steel plate ($-28$ V dc), with a 0.635 cm i.d. orifice, allows the mass spectrometer chamber to be maintained at $2\times 10^{-6}$ Torr using a 550 L/s turbomolecular pump. The 2000 amu range quadrupole mass filter, Extrel Co. (Pittsburgh, PA), Model CQPS1HV, and a channeltron electron multiplier 74, Detector Technologies, Inc. (Brookfield, MA), Model 203, operated in the analog mode. Data acquisition and mass scanning was performed with a Teknivent Corp. (St. Louis, MO) Model 1050 interface-IBM PC/XT based system. Additional operational parameters were as follows: applied voltage of 40,000 V dc, electrospray voltage of 3,000 V dc, focus ring voltage of 190 V dc, $N_2$ flow rate of 2.5 L/min, source temperature of 60 TM C, RF only quadrupole dc bias of $-1.8$ V dc, and an ion entrance aperture of $-28$ V dc.

Injection of samples onto the CZE capillary was performed using the previously-described electromigration technique of Jorgenson et al. In electromigration, the anode end 39 of the column is introduced into the analyte solution, the injection voltage is turned on for a predetermined amount of time, the voltage is turned off and the buffer replaced; the CZE applied voltage ($V_{app}=40,000$ V dc) and electrospray voltage ($V_{ESI}=3000$ V dc) are then turned on and the separation is allowed to continue. (The CZE voltage ($V_{CZE}$) here refers to the voltage drop across the CZE column which has been modified from the traditional sense because the cathode is maintained at the electrospray voltage; thus $V_{CZE}=V_{app}-V_{ESI}$.)

A (50—50) water-methanol with $10^{-4}$ M KCl was used as the separation and electrospray medium. It was observed that water-methanol provides a considerable electroosmotic mobility ($3.6\times 10^{-4}$ cm$^2$/V s) with the fused silica capillary. Thus, positively ionized compounds elute in less than 12.5 minutes from a 100 cm long column (with $V_{CZE}=37,000$ V).

RESULTS AND DISCUSSION

Five ammonium salts were tested: tetramethyl ammonium bromide, tetraethyl ammonium perchlorate, tetrapropyl ammonium hydroxide, tetrabutyl ammonium hydroxide, and trimethyl phenyl ammonium iodide. These quaternary ammonium salts all give good electrospray signals with the dominant peak in the mass spectrum being the quaternary ammonium cation.

Figure 1:
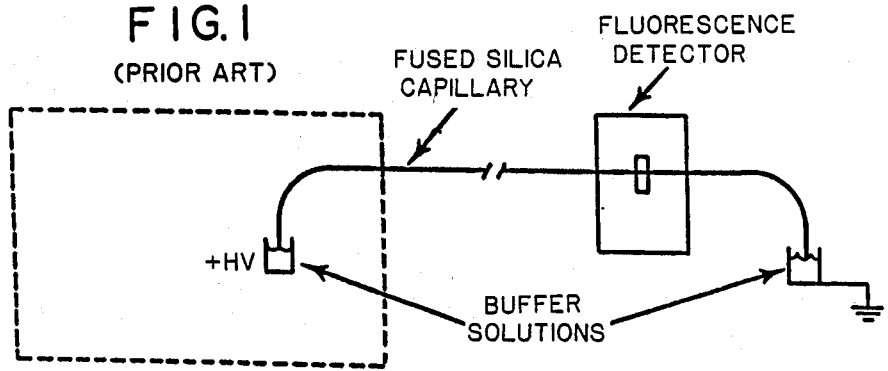
FIG. 1 is a schematic illustration of conventional apparatus used for capillary zone electrophoresis.
Figure 4:
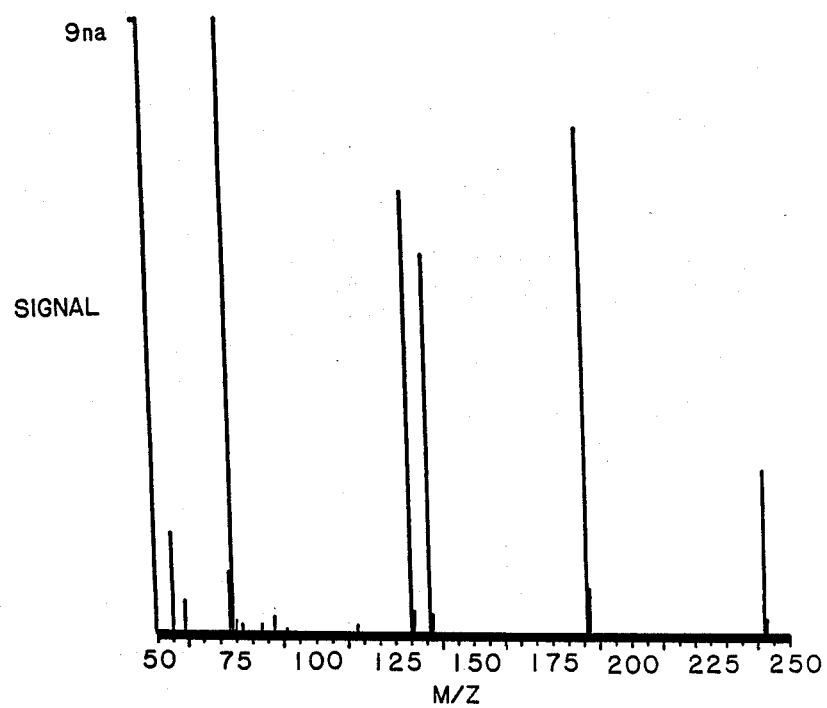
FIG. 4 is an electrospray ionization mass spectrum of a mixture of five quaternary ammonium salts at $10^{-5}$ M concentration introduced by continuous electromigration.

FIG. 4 shows the electrospray ionization mass spectrum for the five components injected at $10^{-5}$ M concentration by continuous electromigration without CZE separation. The dominant peaks are due to the quaternary ammonium cations of: tetramethyl ammonium bromide (m/z-74); tetraethyl ammonium perchlorate (m/z-130); trimethyl phenyl ammonium iodide (m/z=136); tetrapropyl ammonium hydroxide (m/z=186); tetrabutyl ammonium hydroxide (m/z=242); and a background peak due to Na-MeOH+(m/z=55).

Figure 5:
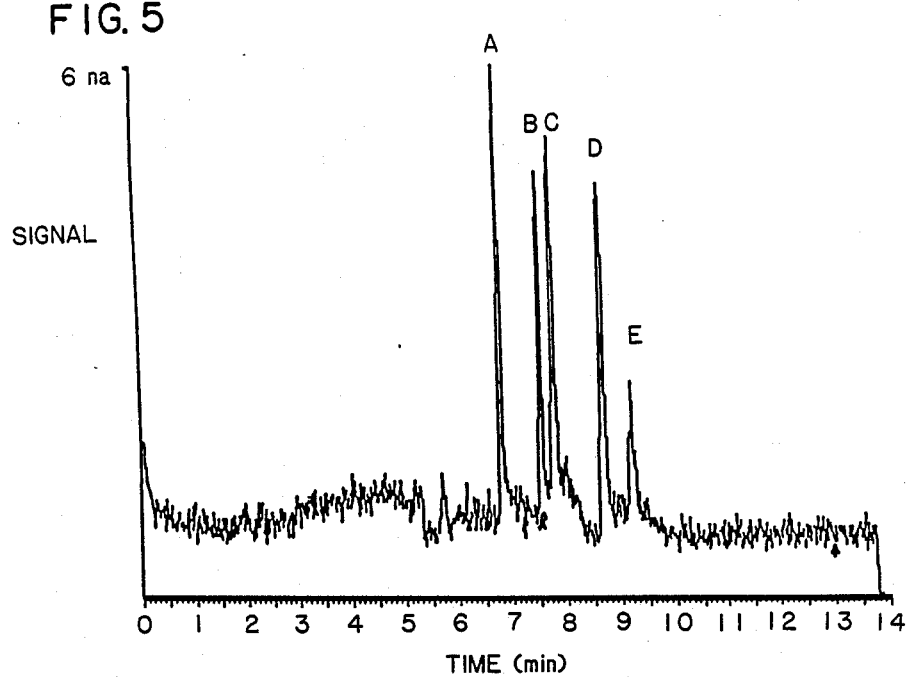
FIG. 5 is an electropherogram, obtained by CZE-MS in accordance with the invention, of five quaternary ammonium salts, at $10^{-6}$ M (14–17 femtomole injection) concentration.

The first CZE-MS separation of such a mixture, taken under multiple ion monitoring of the corresponding quaternary ammonium cation peaks, is shown in FIG. 5. FIG. 5 is an electropherogram of five quaternary ammonium salts, at $10^{-6}$ M (14-17 femtomole injection) concentration, obtained by CZE-MS: (A) tetramethyl ammonium bromide; (B) trimethyl phenyl ammonium iodide; (C) tetraethyl ammonium perchlorate; (D) tetrapropyl ammonium hydroxide; (E) tetrabutyl ammonium hydroxide. The amounts injected for the quaternary ammonium salts, 14-17 femtomoles, gave single ion electropherograms with good peak shapes and signal/noise ratios.

Figure 6:
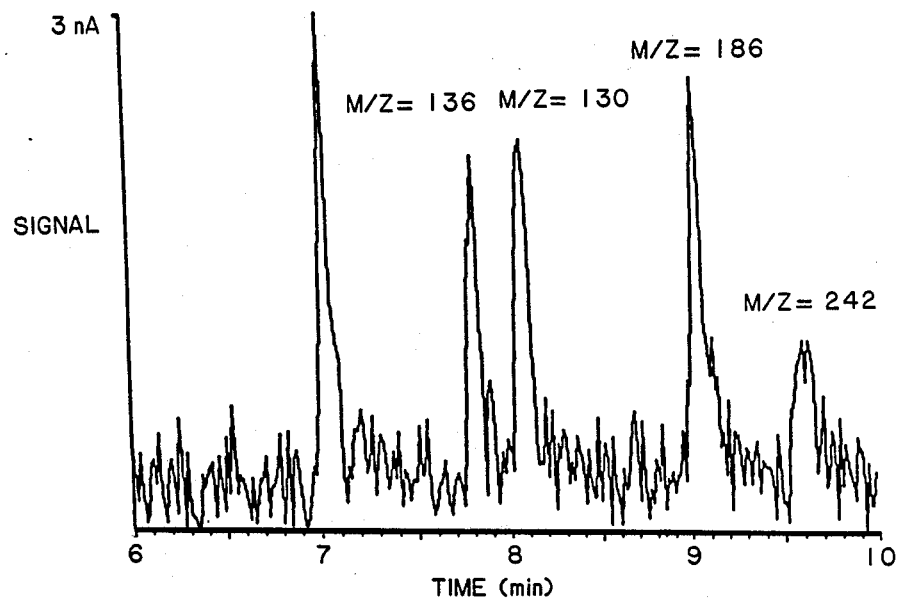
FIG. 6 is an electropherogram, obtained by CZE-MS in accordance with the invention, of five quaternary ammonium salts, at $10^{-7}$ M (0.7–0.9 femtomole injection) concentration.

FIG. 6 is an electropherogram of five quaternary ammonium salts, at $10^{-7}$ M (0.7-0.9 femtomole injection) concentration, obtained by CZE-MS: tetramethyl ammonium bromide (m/z-74); tetraethyl ammonium perchlorate (m/z-130); trimethyl phenyl ammonium iodide (m/z 136); tetrapropyl ammonium hydroxide (m/x=186); tetrabutyl ammonium hydroxide (m/z - 242). FIG. 6 shows the same separation obtained for a 0.7-0.9 femtomole injection, obtained by decreasing $V_i$ to 20,000 V, and C to $10^{-7}$M.

Though the separation efficiencies in FIG. 5 vary from 26,000 and 100,000 theoretical plates, they are increased to between 35,000 and 140,000 theoretical plates in FIG. 6. Such increases in efficiency with decrease in sample concentration and size suggest further improvement can be obtained with higher buffer ionic strength and either smaller diameter or longer capillaries.

As described earlier, the cathode need not be in a buffer reservoir, but only biased negative with respect to the anode. Thus, a metallized segment of capillary tubing or other electrical contact with the buffer provides the essential control of the electric field. This approach (necessary for mass spectrometric interfacing) does not alter the electroosmotic flow, if a pressure drop along the length of the capillary is avoided, at least to an extent that is detectable with fluorescence detection just prior to the electrospray. The success of this approach is further supported by the high efficiency separations presented. On the basis of these results, electrospray ionization appears to provide an ideal interface for the combination of a highly efficient separation technique, CZE, with the sensitive and highly specific detector provided in the mass spectrometer.

Complex mixtures of compounds pose a problem even to the trained mass spectroscopist because the identity and the quantity of each constituent is not readily ascertainable.

Figure 8:
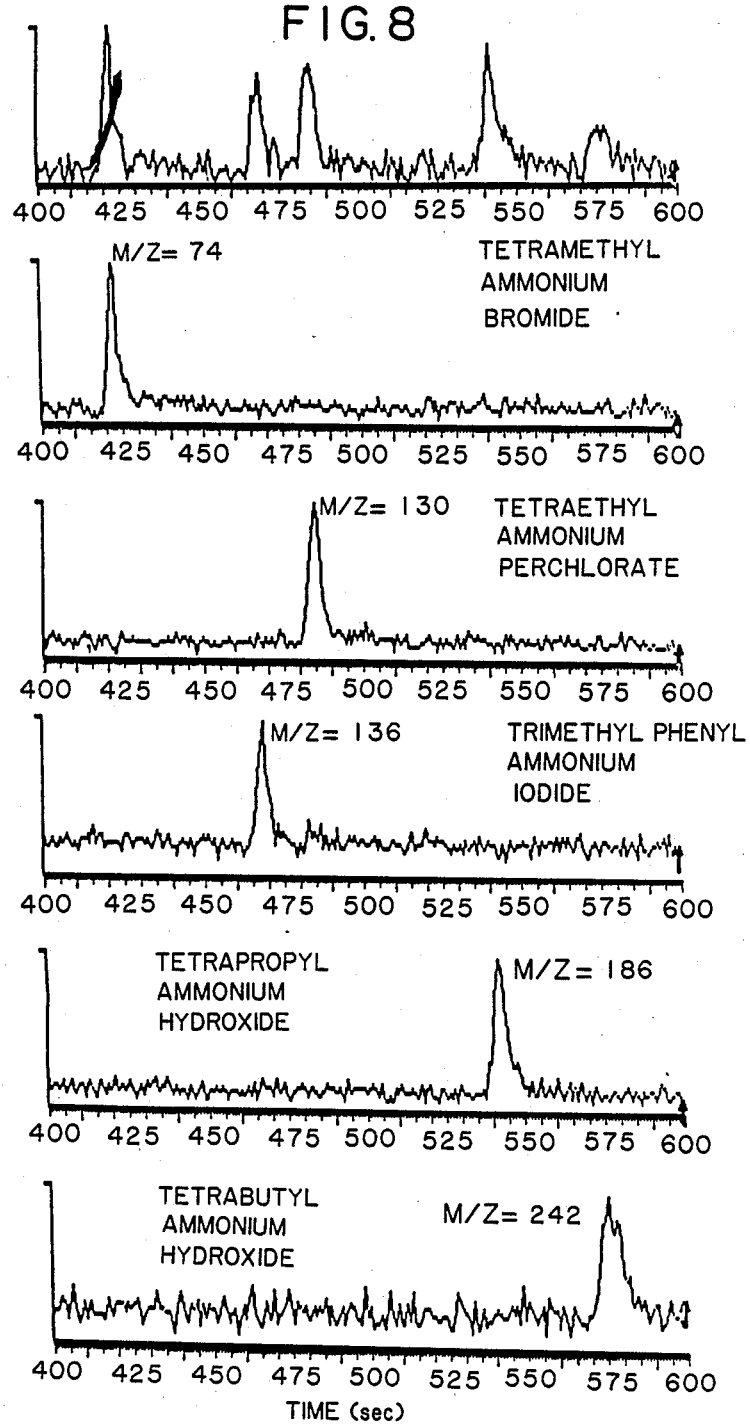
FIG. 8 is a set of total ion and single-ion electropherograms of five quaternary ammonium salts obtained by CZE-MS in accordance with invention.
Figure 9:
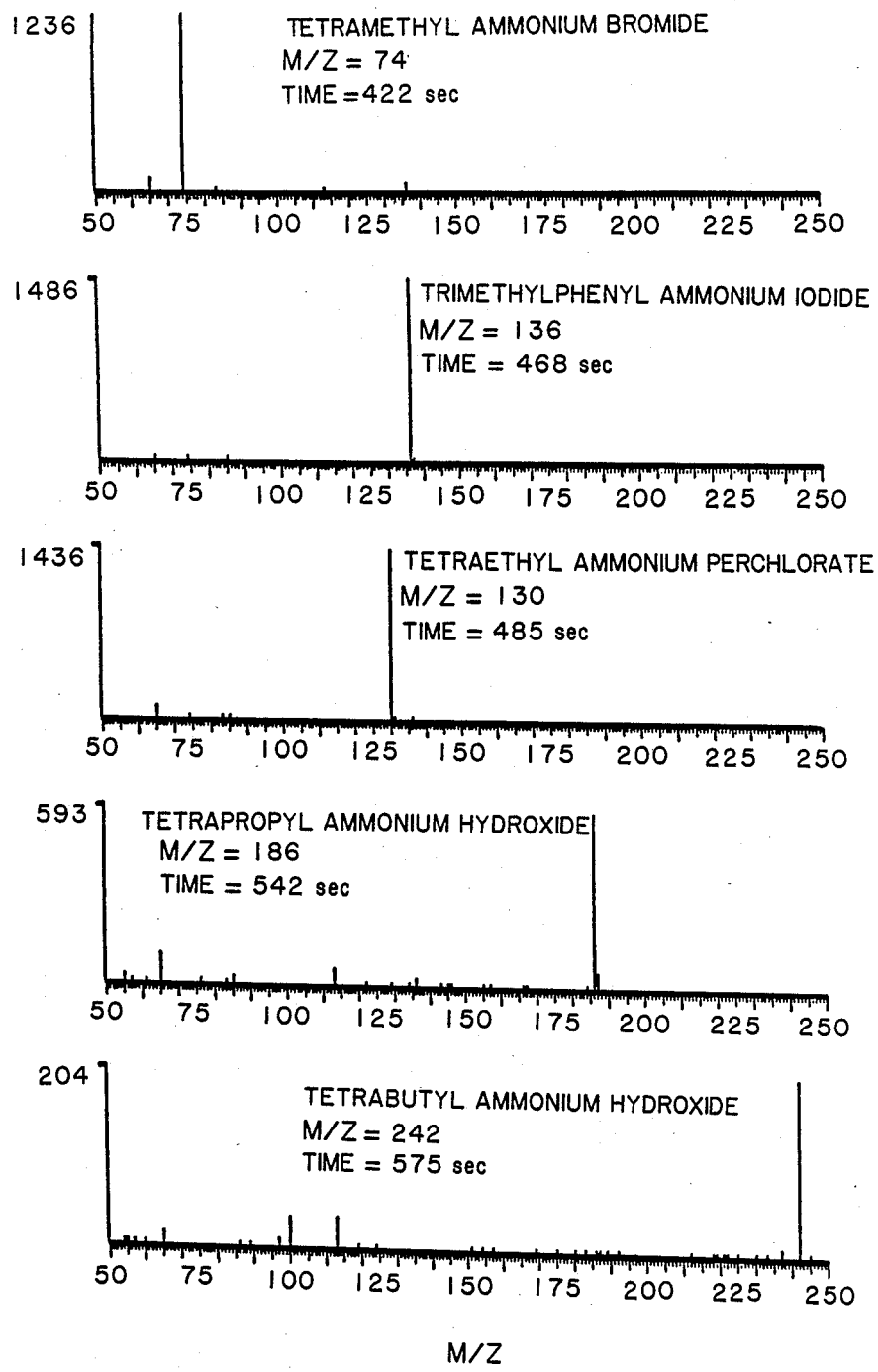
FIG. 9 is a set of mass spectra of CZE-MS separated compounds of the quaternary ammonium salt mixture of the electropherogram of FIG. 6.

Using the system and method of the present invention, a series of electropherograms of the abovedescribed five quaternary ammonium salts were produced (see FIG. 8). These electropherograms are obtained by tracing the ion current for a particular ion of mass m/z throughout the separation process (over time). Single mass spectra (see FIG. 9) for each of the components to be determined can then be obtained for a particular time in the separation process. These mass spectra are used to identify the molecular weight of the particular component, while the area under the electropherogram peak is used for quantification.

Having illustrated and described the principles of our invention in a preferred embodiment thereof, it should be readily apparent to those skilled in the art that the invention can be modified in arrangement and detail without departing from such principles. The extension of CZE, electrokinetic chromatography or isotachophoresis interfaced using the described electrospray process to other analytical or detection devices as well as off-line sample collection is also part of this invention. We claim all modifications coming within the spirit and scope of the accompanying claims.

We claim:

1. A method of producing high resolution analyte separations capable of being analyzed by numerous analytical detectors, which comprises:

providing a source of an analyte sample solution;

electrophoretically separating said analyte sample solution to form a high resolution analyte eluent; and electrospraying the separated analyte eluent into near atmospheric pressure as it elutes from the electrophoretic separation to form an electrically-charged spray.

2. The method of claim 1, which includes conducting said electrophoretic separation of the sample solution in an electrically nonconductive capillary, providing a conductive means for electrically contacting the eluent adjacent the outlet of said capillary, and coupling said conductive means in a high voltage circuit means for electrophoretically separating the sample solution and electrospraying the separated analyte eluent.

3. The method of claim 2, which includes applying a high voltage potential to the sample solution between the source and the conductive means to drive said electrophoretic separation.

4. The method of claim 2, which includes applying a voltage potential between the conductive means and a detector or collector spaced in proximity thereto for electrospraying said separated analyte eluent.

5. The method of claim 1, which includes conducting said electrophoretic separation in a nonconductive capillary, and electrospraying said separated analyte eluent as it emanates from an exit of said capillary.

6. The method of claim 1, which includes conducting said electrophoretic separation in a nonconductive capillary, electrospraying said separated analyte eluent from the outlet of said capillary, and electrically connecting said capillary outlet so as to form both an electrode for electrophoretically separating said analyte sample solution and an electrospray source for electrospraying said separated analyte eluent.

7. The method of claim 1, which includes directly imparting an electrical potential to the analyte eluent immediately prior to said electrospraying, without substantial distortion of the analyte electropherogram, so that the electrosprayed eluent maintains said high resolution separation for analytical determination of the identity and the quantity of the constituents forming said analyte sample by numerous analytical detectors.

8. The method of claim 1, which includes conducing said electrophoretic separating, said direct electrical charging, and said electrospraying with a minimum effective dead volume so that electroosmotic flow of the analyte is provided with a minimum introduction of any turbulent effects.

9. The method of claim 8, wherein the effective dead volume is not more that about 1 nL.

10. The method of claim 1, in which the electrophoretic separation is performed at a substantially constant pressure.

11. The method of claim 1, in which the analytical detector is a mass spectrometer, the electrospraying step including biasing the analyte eluent at a voltage relative to the mass spectrometer sufficient to produce an ionized spray and sampling the ionized spray using mass spectrometry.

12. The method of claim 11 including reducing the pressure, after sampling the ionized spray, in stages prior to analysis.

13. The method of claim 11 including desolvating the ionized spray to form a gas phase ionic spray for sampling.

14. The method of claim 13 including focusing the sampled portion of the gas phase ion spray into the entrance to the mass spectrometer.

15. A system for producing high resolution separation of analyte composition for analysis by an analytical detector, which comprises:
a source of an analyte sample solution;
means for electrophoretically separating said analyte sample solution to form a high resolution analyte eluent; and
means for electrospraying said separated analyte eluent into near atmospheric pressure without substantial distortion of the analyte separation.

16. The system of claim 15, which includes means for directly imparting an electrical potential to said separated analyte eluent immediately prior to said electrospraying.

17. The system of claim 15, which includes an electrically nonconductive capillary for conducting said electrophoretic separation, and electrical contact means disposed in an outlet end of said capillary for forming an electrical contact with said separated analyte eluent.

18. The system of claim 17, which further includes a first high voltage supply coupled to said electrical contact means to form a first high voltage circuit through said analyte eluent for electrophoretically separating same.

19. The system of claim 17, which further includes a second voltage supply coupled to said electrical contact means to form a second voltage potential between the analyte eluent and a detector or collector spaced in proximity to said outlet end for electrospraying the eluent.

20. The system of claim 15, which includes an electrically nonconductive capillary for conducting said electrophoretic separation, said capillary including an outlet section which comprises conductive means defining both an electrode for electrophoretically separating said analyte sample solution and an electrospray source for electrospraying said separated analyte eluent.

21. The system of claim 20, wherein said outlet section includes a conductive end suction joined thereto and located concentrically about an exit of the capillary for electrically contacting said eluting analyte.

22. The system of claim 20, wherein said conductive end section comprises a conductive metal coating deposited on an end portion of the capillary including an axial end portion thereof.

23. The system of claim 20, wherein said electrophoretic separating means and said conductive means are arranged to define a continuous flow surface having minimum effective dead volume so that electroosmotic flow of the analyte is provided with a minimum introduction of turbulence.

24. The system of claim 20, including:
detector means for detecting constituents of a spray of the analyte solution;
a first voltage supply means coupled to said conductive means for applying a first high voltage potential between the source and the electrode to electrophoretically separate the analyte sample; and
a second voltage supply means coupled to said conductive means for applying a second voltage potential between the electrospray needle and the detector means.

25. The system of claim 24 in which the detector means is a mass spectrometer.

26. The system of claim 25 in which the mass spectrometer is spaced from the outlet section of the capillary by an airgap through which the analyte eluent is electrosprayed.

27. The system of claim 14 in which the airgap defines the region of near atmospheric pressure and the mass spectrometer includes a differentially pumped input chamber.

28. The system of claim 26 including means for desolvating the electrospray to produce a gas phase ion spray for sampling by the mass spectrometer.

29. The system of claim 28 including means defining an ion lens for focusing a sampled portion of the gas phase ion spray into the mass spectrometer.

30. A method for producing and detecting high resolution separations of analyte compositions which comprises:
providing a source of buffer solution and a source of a sample solution composed of a mixture of constituents, each said constituent having a different electrophoretic mobility;
proving an open tubular capillary having an inlet end and an outlet end and formed of a nonconductive material capable of establishing an electroosmotic flow of said solution;
filling the capillary with the buffer solution;
introducing a small amount of the sample solution at the inlet end of the capillary;
placing the inlet end of the capillary in the buffer solution;
applying a first high voltage potential to the buffer solution between the inlet end and outlet end of the capillary for electrophoretically separating said sample mixture into its sample constituents, each said constituent migrating in accordance with its electrophoretic mobility from said inlet end to the outlet end of said capillary at a different time interval;
coupling a second voltage potential directly to said separated sample at said outlet end for electrospraying said separated constituents into near atmospheric pressure, each constituent being electrosprayed at a time interval determined by the electrophoretic separation; and detecting and analyzing the identity and the quantity of the constituents forming said sample mixture in accordance with said time intervals.

31. A method for analyzing molecular constituents of a sample composed of a plurality of constituents, each said constituent having a different electrophoretic mobility, comprising:

forming a solution of the sample;

separating the solution by capillary zone electrophoresis into an eluent of the constituents longitudinally separated according to their relative electrophoretic mobilities;

electrospraying the eluent into near atmospheric pressure to form a charged spray in which the molecular constituents have a temporal distribution; and detecting or collecting the separated constituents in accordance with the temporal distribution in the spray.

32. A method according to claim 31 including forming a complete electrical circuit, including a conductor which directly contacts the eluent at the capillary exit, for electrophoretically separating the sample and electrospraying the separated eluent.

33. A method according to claim 31 including desolvating the charged spray to remove a solvent from the electrosprayed, electrophoretically-separated solution.

34. A method according to claim 23 including removing all of the solvent to produce a gaseous spray of electrophoretically-separated ions.

35. A method according to claim 31 in which detecting and analyzing includes mass spectroscopy.

36. A method according to claim 35 including forming a quadrupole ion lens for constraining the sprayed ions to an axial flow path.

37. A method of producing high resolution analyte separations capable of being analyzed by numerous analytical detectors, which comprises:

providing a source of an analyte sample solution;

electrophoretically separating said analyte sample solution in an electrically nonconductive capillary having an inlet and outlet to form a high resolution separated analyte eluent, including providing a conductive means for electrically contacting the eluent adjacent the outlet of said capillary and applying a first voltage potential to the sample solution between the source and the conductive means to drive said electrophoretic separation; and electrospraying the separated analyte eluent into near atmospheric pressure to form an electrically-charged spray, including applying a second voltage potential between the conductive means and a detector or collector spaced in proximity thereto for electrospraying said separated analyte eluent as it emanates from the outlet of said capillary.

38. A method according to claim 37 including maintaining a pressure around both the inlet and outlet of the capillary at about atmospheric pressure so as to minimize pressure drop between the capillary inlet and outlet and to produce ions in the spray.

39. A system for producing high resolution separation of analyte composition for analysis by an analytical detector, which comprises:

a source of an analyte sample solution;

means for electrophoretically separating said analyte sample solution to form a high resolution separated analyte eluent, including an electrically nonconductive capillary having an inlet end and an outlet end for conducting said electrophoretic separation, electrical contact means disposed in the outlet end of said capillary for forming an electrical contact with said separated analyte eluent, and a first high voltage supply coupled to inlet end and outlet end of the capillary via said electrical contact means to form a first high voltage circuit through said analyte eluent for electrophoretically separating same; and means for electrospraying said separated analyte eluent into near atmospheric pressure without substantial distortion of the analyte separation, including a second voltage supply coupled to said electrical contact means to form a second voltage potential between the analyte eluent and a detector or collector spaced in proximity to said outlet end for electrospraying the eluent;

the first and second voltage supplies being coupled in a common electrical circuit in which the electrical contact means at the outlet of the capillary forms an electrical node between the first and second voltage potentials.

40. An electrophoretic mass spectrometric process in which chemical components are separated from complex mixtures and analyzed in real-time to yield molecular weights and structural information of the electrophoretically separated chemicals, the process comprising the steps of:

directing a quantity of electrically conducting buffer material into a capillary tube;

directing a mixture to be separated and analyzed into the buffer material in the capillary tube;

impressing an electrical potential on said capillary tube;

separating chemicals from the mixture by electrophoresis as the mixture migrates along the interior of the capillary;

electrospraying the separated components directly from an outlet of the capillary into a near-atmospheric pressure region to form a spray of ions;

directing a portion of the spray of ions through an orifice into a vacuum region of a mass spectrometer.

41. A process according to claim 40 in which impressing an electrical potential on the capillary tube includes applying a first electrical potential from the capillary outlet to a capillary inlet to drive the electrophoresis and electrospraying the separated components includes applying a second electrical potential from the capillary outlet to a counter-electrode spaced from the capillary outlet between the near atmospheric-pressure region and the vacuum region of the mass spectrometer, the capillary outlet forming a common node for the first and second voltage potentials.

* * * * *

UNITED STATES PATENT AND TRADEMARK OFFICE
CERTIFICATE OF CORRECTION

PATENT NO.   : 4,842,701

DATED        : June 27, 1989

INVENTOR(S)  : Smith et al.

It is certified that error appears in the above-identified patent and that said Letters Patent is hereby corrected as shown below:

| | |
|---|---|
| Title page, | in Other Publications, line 3, change "Nov." to --No.--; |
| Column 2, | line 22, change "carried" to --carrier--; |
| | line 58, change "spectrometry," to --spectrometry--; |
| Column 4, | line 33, change "of" to --or--; |
| | line 40, after "16B" insert --,--; |
| Column 5, | line 66, before "solution" insert --buffer--; |
| Column 6, | line 48, change "negative" to --negatively--; |
| Column 7, | line 26, change "along" to --alone--; |
| Column 11, | line 26, change "offline" to --off-line--; |
| Column 12, | line 42, change "60 TM C," to --60C,--; |
| Column 14, | lines 2 & 3, change "abovede-scribed" to --above-described-- |
| Column 15, | line 4, change "conducing" to --conducting--; |

UNITED STATES PATENT AND TRADEMARK OFFICE
CERTIFICATE OF CORRECTION

PATENT NO. : 4,842,701

DATED : June 27, 1989

INVENTOR(S) : Smith et al.

It is certified that error appears in the above-identified patent and that said Letters Patent is hereby corrected as shown below:

Column 15,    line 68, change "suction" to --section--;

Column 16,    line 30, change "14" to --26--;

line 47, change "proving" to --providing--;

Column 17,    line 30, change "23" to --33--.

Signed and Sealed this

Sixteenth Day of July, 1991

Attest:

HARRY F. MANBECK, JR.

Attesting Officer     Commissioner of Patents and Trademarks